United States Patent
Zhang (10) Patent No.: US 8,903,480 B2
(45) Date of Patent: Dec. 2, 2014

(54) SYSTEM FOR CARDIAC CONDITION DETECTION USING HEART WAVEFORM AREA ASSOCIATED ANALYSIS

(71) Applicant: Hongxuan Zhang, Palatine, IL (US)

(72) Inventor: Hongxuan Zhang, Palatine, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 11 days.

(21) Appl. No.: 13/741,414

(22) Filed: Jan. 15, 2013

(65) Prior Publication Data

US 2013/0274623 A1 Oct. 17, 2013

Related U.S. Application Data (60) Provisional application No. 61/622,685, filed on Apr. 11, 2012.

(51) Int. Cl.
*A61B 5/0452* (2006.01)
*A61B 5/04* (2006.01)
*A61B 5/00* (2006.01)
*A61B 5/021* (2006.01)
*A61B 5/1455* (2006.01)

(52) U.S. Cl.
CPC ............ *A61B 5/04012* (2013.01); *A61B 5/0452* (2013.01); *A61B 5/7264* (2013.01); *A61B 5/021* (2013.01); *A61B 5/14551* (2013.01)
USPC .......................................... 600/517; 600/516

(58) Field of Classification Search
CPC . A61B 5/0452; A61B 5/04525; A61B 5/0456
USPC ...................................................... 607/16, 17
See application file for complete search history.

(56) References Cited

U.S. PATENT DOCUMENTS

| | | | |
|---|---|---|---|
| 4,681,117 A | 7/1987 | Broadman et al. |
| 4,798,211 A | 1/1989 | Goor et al. |
| 4,924,875 A | 5/1990 | Chamoun |
| 4,930,075 A | 5/1990 | Kortas |
| 5,054,496 A | 10/1991 | Wen et al. |
| 5,159,932 A | 11/1992 | Zanetti et al. |
| 5,365,426 A | 11/1994 | Siegel et al. |
| 6,024,705 A | 2/2000 | Schlager et al. |
| 6,112,116 A | 8/2000 | Fischell et al. |
| 6,339,720 B1 | 1/2002 | Anzellini et al. |
| 6,368,284 B1 | 4/2002 | Bardy |
| 6,424,860 B1 | 7/2002 | Karlsson et al. |
| 6,468,263 B1 | 10/2002 | Fischell et al. |
| 6,501,983 B1 | 12/2002 | Natarajan et al. |
| 6,663,572 B2 | 12/2003 | Starobin et al. |
| 7,072,708 B1 | 7/2006 | Andresen et al. |

(Continued)

*Primary Examiner* — Joseph Dietrich
(74) *Attorney, Agent, or Firm* — Brennan K Bradley (57) ABSTRACT

A system for heart performance characterization uses an interface to receive waveform signal data representing electrical activity of a patient heart over at least one heart beat cycle. The signal processor uses a signal peak and amplitude detector for, identifying a first signal portion of a first heart cycle of the signal data, identifying multiple different amplitude levels within the first signal portion, determining a first area under the waveform in the first signal portion corresponding to at least one particular amplitude level and deriving a parameter in response to the determined first area. The output processor generates an alert message if at least one of, (a) the derived parameter and (b) a difference between the derived parameter and a corresponding derived parameter for a different heart cycle for the same patient, exceeds a predetermined threshold value.

21 Claims, 7 Drawing Sheets

Example of QRS complex waveform portion for segmentation

(56) References Cited

U.S. PATENT DOCUMENTS

| | | |
|---|---|---|
| 7,181,268 B2 | 2/2007 | Sheldon et al. |
| 7,225,013 B2 | 5/2007 | Geva et al. |
| 7,225,015 B1 | 5/2007 | Min et al. |
| 7,231,244 B2 | 6/2007 | Laitio et al. |
| 7,266,410 B2 | 9/2007 | Chen |
| 7,277,745 B2 | 10/2007 | Natarajan et al. |
| 7,361,473 B2 | 4/2008 | Valkirs et al. |
| 7,415,307 B2 | 8/2008 | Sharma et al. |
| 7,654,965 B2 | 2/2010 | Morganroth |
| 7,813,792 B2 | 10/2010 | Xue et al. |
| 7,869,864 B2 | 1/2011 | Tseng et al. |
| 7,904,153 B2 | 3/2011 | Greenhut et al. |
| 7,996,070 B2 | 8/2011 | Van Dam et al. |
| 8,010,347 B2 | 8/2011 | Ricci et al. |
| 8,024,030 B2 | 9/2011 | Douglas et al. |
| 2006/0041201 A1* | 2/2006 | Behbehani et al. ............ 600/521 |
| 2009/0259266 A1 | 10/2009 | Zhang et al. |
| 2009/0281441 A1 | 11/2009 | Zhang et al. |
| 2012/0179055 A1* | 7/2012 | Tamil et al. ................... 600/509 |

* cited by examiner

SYSTEM FOR CARDIAC CONDITION DETECTION USING HEART WAVEFORM AREA ASSOCIATED ANALYSIS

This is a non-provisional application of provisional application Ser. No. 61/622,685 filed Apr. 11, 2012, by H. Zhang.

FIELD OF THE INVENTION

This invention concerns a system for heart performance characterization by determining an area within a predetermined amplitude level partition of a portion of a heart electrical activity waveform within a heart cycle.

BACKGROUND OF THE INVENTION

Cardiac electrophysiological activity analysis is used for the management of cardiac disorders and irregularities, such as ventricular myocardial ischemia caused by a lack of blood and oxygen, in heart tissue. Usually, skin surface ECG signal analysis based on waveform time domain parameters is utilized for cardiac arrhythmia detection and characterization, including heart rate variability (HRV), cardiac wave morphology, R wave-ST segment and T wave amplitude analysis. However known cardiac status detection and characterization systems fail to determine severity and quantitatively characterize ongoing ischemia events and are subjective and need extensive clinical expertise and knowledge for accurate use. Inaccurate and subjective evaluation and diagnosis may cause unexpected delay in cardiac rhythm management, drug delivery and emergency treatment.

A 12-lead electrocardiogram (ECG) and multi-channel intra-cardiac electrograms (ICEG) are used for evaluating cardiac rhythm and events. Known waveform morphology parameter analysis systems, such as P wave, QRS complex, ST segment, T wave analysis systems, are used for cardiac arrhythmia monitoring and identification, e.g., of atrial fibrillation (AF), myocardial ischemia (MI) and ventricular tachycardia/fibrillation (VT/VF). However, known waveform morphology parameter analysis is often subjective and time-consuming, and requires extensive medical expertise and clinical experience for accurate interpretation and proper cardiac rhythm management. Additionally, cardiac electrophysiological activity and signals (ECG and ICEG) are time varying and known signal analysis typically cannot localize a precise malfunction and severity of cardiac events (e.g., myocardial ischemia and infarction), and different stages of cardiac pathology irregularity and arrhythmia.

Known clinical methods use electrophysiological (EP) surface ECG and ICEG signal voltage amplitude analysis for arrhythmia detection to identify and characterize cardiac abnormality and arrhythmia related information (such as timing, energy). Known clinical diagnosis standards may be of limited value in some cases. For example, myocardial ischemia and infarction detection is usually based on ST segment voltage deviation for ischemia event detection (e.g. 0.1 mV elevation). However this only works for surface ECG signals not for intra-cardiac electrograms (ICEG signals). Known methods for cardiac arrhythmia analysis, such as myocardial ischemia event detection and evaluation, rely on a repolarization signal portion, such as ST segment and T wave morphology changes. Known methods lack capability for quantitative characterization of cardiac arrhythmia severity and may cause a false alarm. For example amplitude voltage ST segment measurement fails to provide a reliable severity level of an ischemia event. Heart rate variability is unable to provide an arrhythmia urgency level. A system according to invention principles addresses these deficiencies and related problems and provides an earlier more accurate detection and characterization of a cardiac arrhythmia event and can be used in an ICD (intra-cardiac device), for example.

SUMMARY OF THE INVENTION

A system analyzes cardiac electrophysiological signals (including ECG and ICEG signals) by calculation of ratios (time-spatial ratio, area ratio, energy ratio) between a repolarization portion and depolarization portion within the same heart beat, for real time monitoring and analysis of cardiac tissue. A system for heart performance characterization and abnormality detection includes an interface, a signal processor and an output processor. The interface receives waveform signal data representing electrical activity of a patient heart over at least one heart beat cycle. The signal processor uses a signal peak and amplitude detector for, identifying a first signal portion of a first heart cycle of the signal data, identifying multiple different amplitude levels within the first signal portion, determining a first area under the waveform in the first signal portion corresponding to at least one particular amplitude level and deriving a parameter in response to the determined first area. The output processor generates an alert message if at least one of, (a) the derived parameter and (b) a difference between the derived parameter and a corresponding derived parameter for a different heart cycle for the same patient, exceeds a predetermined threshold value.

DETAILED DESCRIPTION OF THE INVENTION

A system analyzes cardiac electrophysiological signals (including surface ECG signals and intra-cardiac electrograms, ICEG signals) using cardiac repolarization and depolarization pattern quantification. In particular the system calculates ratios including time-spatial ratio, area ratio and energy ratio between a repolarization portion and depolarization portion within the same heart beat, for real time monitoring and analysis of cardiac tissue. The system is usable in implantable devices and may employ ratio variability and variation determination to characterize electrophysiological activities and cardiac functions with improved sensitivity and stability, especially in the presence of noise.

The system employs pattern analysis and diagnosis methods based on depolarization and repolarization characteristics of an electrophysiological signal for either atrium or ventricle function analysis and detection of early stage atrial fibrillation and myocardial ischemia-infarction, for example. The system advantageously uses depolarization signals for ischemia and infarction characterization and analyzes depolarization and repolarization EP signal portions by detecting timing, frequency and energy changes to identify heart conditions. The system improves accuracy and reliability in identifying cardiac disorders, differentiating cardiac arrhythmias, characterizing pathological severity, predicting life-threatening events, and evaluating effect of medication.

During ischemia, various portions of heart muscle receive less oxygen leading to irreversible scarring and necrosis of the muscle tissue (myocardial infarction), reducing the efficiency with which the heart can pump blood to the rest of the body and possibly leading to fatal cardiac arrhythmias. Cardiac functional abnormality and arrhythmias usually slow down tissue performance (contracting and reperfusion) and reduce blood flow to regions of the heart, where cells respond by altering the action potentials. The changes in these individual cells manifest in the local electrograms during depolarization and repolarization, reducing signal energy (hyperkalemia or anoxia) or creating multi-phasic waveforms (decoupling). These abnormal behaviors in relatively small regions of the heart, lumped together with the rest of the heart, cause notches and slurs of small amplitude superimposed on largely normal electrograms of surface ECG signals and intra-cardiac signals. Ventricular activity and signal monitoring, of both depolarization and repolarization signals, facilitates detection, characterization and treatment of MI events. The system characterizes different tissue portions by identifying electrophysiological signal pattern ratios associated with heart depolarization and repolarization ECG signal portions for cardiac signal diagnosis and evaluation and early detection, diagnosis and characterization of myocardial ischemia and infarction.

Figure 1:
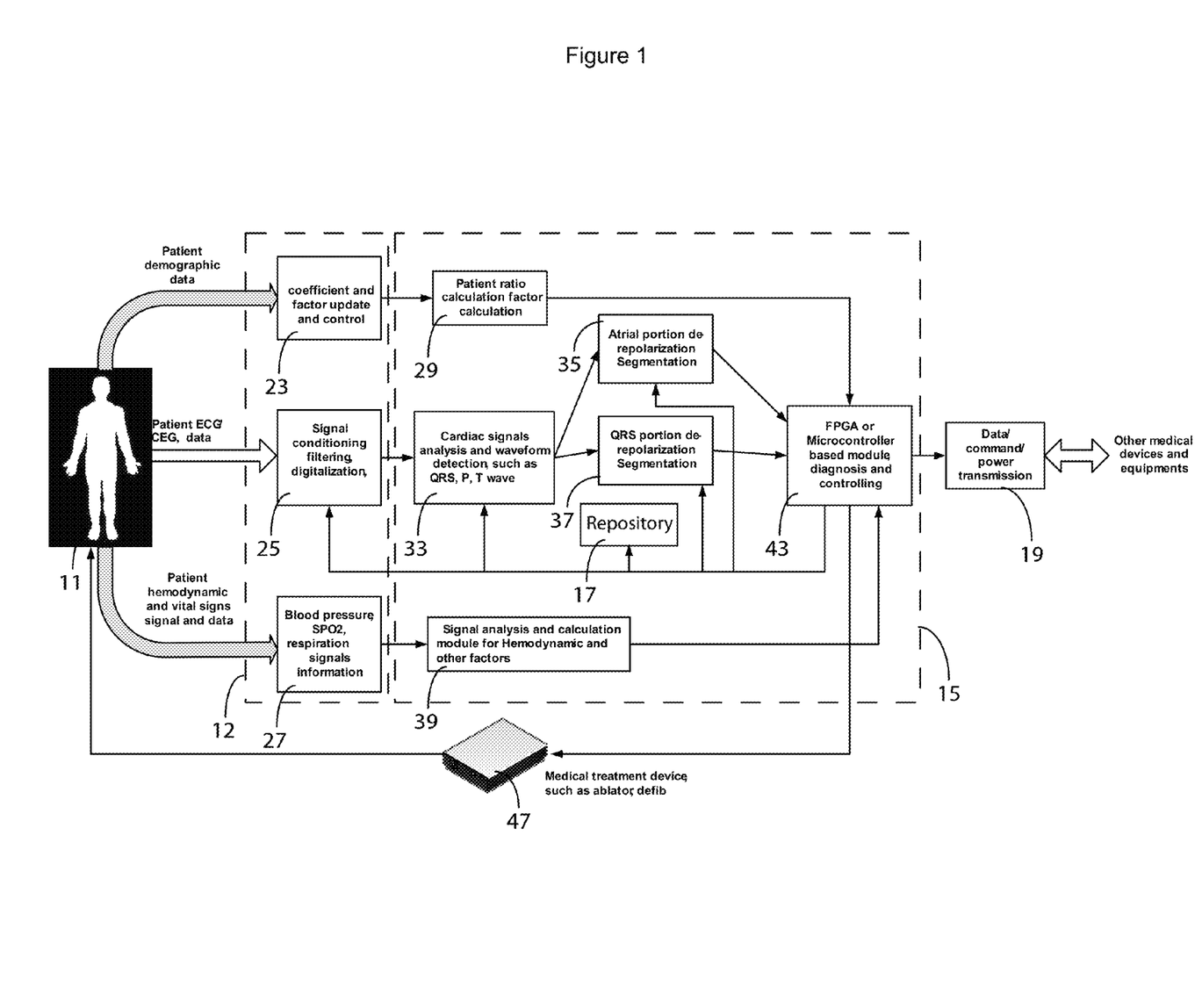
FIG. 1 shows a system for heart performance characterization and abnormality detection, according to invention principles.

FIG. 1 shows system 10 for heart performance characterization and abnormality detection using a closed loop architecture for real time analysis of different portions of a cardiac signal by signal segmentation and depolarization, repolarization pattern ratio analysis. The system is implemented by a computer, microprocessor, programmed logic device or other processing device. Interface 12 includes units 23, 25 and 27. Signal processor 15 comprises units 29, 33, 35, 37, 39 and 43. Demographic data interface 23 processes demographic data of patient 11 and in conjunction with patient ratio calculator 29 determines and updates coefficients and factors used by processor 43 for determining heart condition indicative parameters associated with a heart cycle. Vital sign interface 27 processes patient 11 vital sign data including blood pressure, respiration and blood oxygen saturation (SPO2) signal data that is subsequently analyzed by unit 39 to determine and update coefficients and factors used by processor 43 in determining heart condition indicative parameters associated with a heart cycle.

Signal conditioner 25 buffers, filters and digitizes ECG and ICEG data from patient 11 that are segmented by unit 33. Segmentation unit 33 detects P wave, Q wave, R wave, T wave, S wave and U wave segments of a received signal data by detecting peaks within the received data using a known peak detector and by segmenting the received signal data from unit 25 into windows where the waves are expected and by identifying the peaks within the windows. Unit 37 detects a QRS segment and unit 35 detects an atrial segment in the ECG and ICEG data from unit 25 to derive parameters for depolarization, repolarization analysis by processor 43. Output processor 19 generates an alert message if at least one of, (a) a derived parameter of a heart cycle and (b) a difference between the derived parameter and a corresponding derived parameter for a different heart cycle for the same patient, exceeds a predetermined threshold value. Output processor 19 communicates derived data to other devices.

The start point of a wave, for example, is identified by a variety of known different methods. In one method a wave start point comprises where the signal crosses a baseline of the signal (in a predetermined wave window, for example). Alternatively, a wave start point may comprise a peak or valley of the signal. The baseline of the signal may comprise a zero voltage line if a static (DC) voltage signal component is filtered out from the signal. Segmentation unit 33 includes a timing detector for determining time duration between the signal peaks and valleys. The time detector uses a clock counter for counting a clock between the peak and valley points and the counting is initiated and terminated in response to the detected peak and valley characteristics.

System 10 comprises at least one computer system, workstation, server, microcontroller, microprocessor, logic device or other processing device. Interface 12 receives waveform signal data representing electrical activity of a patient heart over at least one heart beat cycle. Signal processor 15 uses a signal peak and amplitude detector for, identifying a first signal portion of a first heart cycle of the signal data and identifying multiple different amplitude levels within the first signal portion. Processor 43 determines a first area under the waveform in the first signal portion corresponding to at least one particular amplitude level and derives a parameter in response to the determined first area. Processor 43 uses derived parameter values in controlling medical devices 47 such as a defibrillator and ablation device in treating patient 11. Output processor 19 generates an alert message if at least one of, (a) the derived parameter and (b) a difference between the derived parameter and a corresponding derived parameter for a different heart cycle for the same patient, exceeds a predetermined threshold value.

Patient demographic data, hemodynamic data, and vital sign signals are processed by system 10 to calculate parameters utilized in pattern ratio analysis. Patient electrophysiological signals (Surface ECG and intra-cardiac electrograms) are sampled and acquired after signal filtering and conditioning. A signal peak detector, timing and segmentation module comprising units 33, 35, 37 is used to characterize P wave, R wave and T waves. Wave segmentation is used to identify different signal portions, such as an Atrial signal portion and QRS complex portion, using amplitude or magnitude segmentation, for example. Different kinds of pattern ratios are calculated by processor 43, including unilateral and bilateral depolarization-repolarization ratios. The depolarization-repolarization signal analysis provides heart condition severity, type, location and priority and processor 43 sends control and treatment information and commands to external medical device 47, such as a pacing, ablator, defibrillator device. The information and data is exchanged with other medical devices. Derived ratios and identified medical conditions and mapping information for ratio to medical condition mapping are stored in repository 17.

Figure 2:
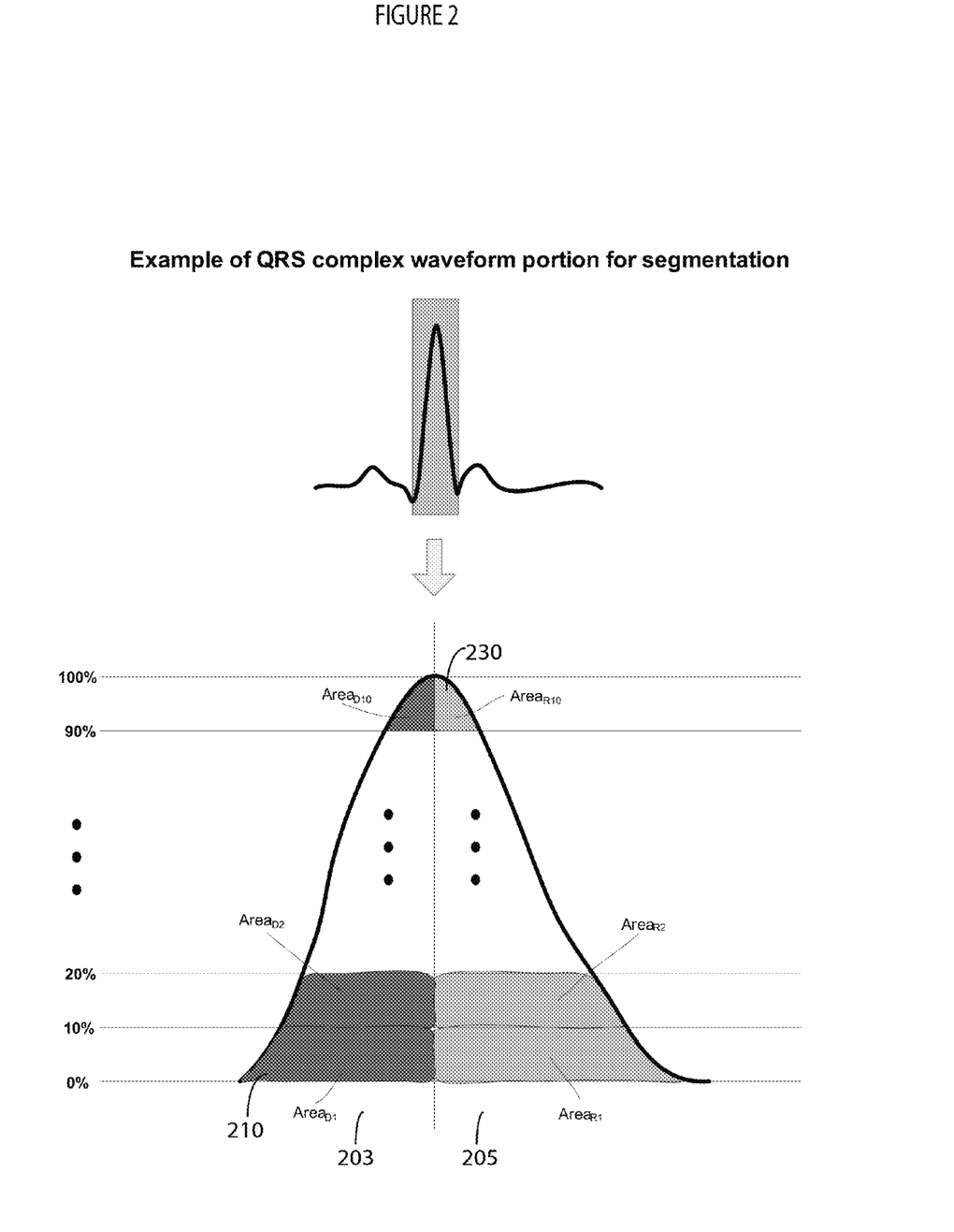
FIG. 2 shows a QRS complex waveform (ventricular depolarization-repolarization) signal segmentation with ten amplitude level partitions, according to invention principles.

FIG. 2 shows QRS complex waveform (ventricular depolarization-repolarization) signal segmentation with ten amplitude level partitions, for example. System 10 (FIG. 1) uses advantageous depolarization and repolarization segmentation and pattern analysis functions and pattern ratio analysis to capture small changes within an ECG waveform. System 10 uses different ways to segment a signal waveform, such as using timing window segmentation, frequency bandwidth segmentation and signal probability segmentation, for example. In an embodiment, a QRS waveform area is segmented into two portions 203, 205 corresponding to, depolarization (rising) and repolarization (falling) procedures, which correspond to electrophysiological processes, a cardiac tissue contraction procedure and blood reperfusion. Signal amplitude is separated into N portions comprising levels which are determined (adaptively and automatically) by the system based on clinical application, noise level, and diagnosis accuracy requirement or manually by a user in an alternative embodiment.

Each segmented area partition represents a segmented electrophysiological process signal portion. For example, $Area_{D1}$ 210 is a first level portion of QRS depolarization while $Area_{R10}$ 232 is a 10th level portion of QRS repolarization. System 10 adaptively selects a number of amplitude levels for a corresponding signal pattern and mode analysis for identifying an abnormal event and early arrhythmia, in response to data indicating a signal portion being analyzed. Different signal portions require different numbers of segmentation levels such as 10 levels for a QRS complex portion, 5 levels for an atrial P wave, for example. The amplitude signal segmentation is different from frequency or other component based segmentation of cardiac signals. The system uses signal segmentation in calculating different pattern ratios including timing ratios, amplitude ratios, area distribution ratios, shape morphology ratios, energy ratios, for example, between a segmented region of interest (ROI) of depolarization and repolarization portions. The system calculates a ratio parameter to provide improved qualitative and quantitative diagnosis of cardiac arrhythmias (especially early stage cardiac abnormal events) as well as to determine malfunction location, arrhythmia severity and pathology type. Both depolarization and repolarization processes are advantageously divided into multiple level areas and segmented portions. Further, the system employs unilateral and bilateral pattern-mode ratios and advantageous equations to quantify and evaluate signals associated with one or both of, depolarization and repolarization.

A depolarization or repolarization procedure in atrial or ventricular chamber tissue is categorized and segmented by processor 43 into different levels within different signal portions for detailed analysis of the signal waveform changes. System 10 determines unilateral pattern ratios comprising area ratios between different amplitude partition levels of a selected ECG signal portion such as a depolarization or repolarization portion.

Depolarization unilateral ratio, $$Ratio\_Depolar_i = \frac{Area_{Di}}{\sum_{j \in N, Depolarization\_level} Area_{Dj}}$$

In which, $Area_{Di}$ is an amplitude level partition in a depolarization area, N is the number of the depolarization segmented level partitions. The segmented area partitions are either within one cardiac cycle or in different heart cycles, Dj is a sum of the amplitude levels containing the Di level.

Repolarization unilateral ratio, $$Ratio\_Repolar_i = \frac{Area_{Ri}}{\sum_{j \in M, Reploarization\_level} Area_{Rj}}$$

In which, $Area_{Ri}$ is an amplitude level in the ROI unilateral repolarization area, M is the number of the repolarization segmented level partitions (in most cases N=M, which is convenient for bilateral and cross ratio analysis). The segmented area partitions are either within one cardiac cycle or in different heart cycles, Rj is a sum of the amplitude levels containing the Ri level. In the unilateral pattern ratio analysis, area size is utilized for segmented signal analysis of either depolarization or repolarization signal portions. Different parameters are used for ratio calculation, such as energy, timing duration, morphology and shape, for example.

Unilateral ratios are ECG signal waveform ratios derived by comparing a signal segmented portion within the same electrophysiological function e.g. depolarization function. In addition to unilateral pattern analysis, bilateral (mutual) pattern ratios and bilateral cross ratios are calculated between depolarization and repolarization signal portions, including energy, area size, timing duration and morphology ratios, for example System 10 determines a Bilateral Depolarization ratio, $$Ratio\_Depolar_{ij} = \frac{Area_{Di}}{Area_{Dj}}$$

In which, $Area_{Di}$ and $Area_{Dj}$ are different amplitude level partitions in a selected segmented level area partition in a depolarization signal portion either within one cardiac cycle or in different heart cycles.

System 10 determines a Bilateral repolarization ratio, $$Ratio\_Repolar_{ij} = \frac{Area_{Ri}}{Area_{Rj}}$$

In which, $Area_{Ri}$ and $Area_{Rj}$ are different amplitude level partitions in a repolarization signal portion either within one cardiac cycle or in different heart cycles. System 10 determines a Bilateral Depolarization-repolarization cross ratio (single level area version), $$Ratio\_De\_Repolar_{ij} = \frac{Area_{Di}}{Area_{Rj}}$$

or $$Ratio\_De\_Depolar_{ij} = \frac{Area_{Ri}}{Area_{Dj}}$$

In which, $Area_{Di}$, $Area_{Rj}$, $Area_{Ri}$, and $Area_{Dj}$ are segmented level area partitions in depolarization and repolarization signal portions either within one cardiac cycle or in different heart cycles.

System 10 determines a Bilateral Depolarization-repolarization cross ratio (multi-level area version), $$Ratio_{Multi}\_De\_Repolar_{nm} = \frac{\sum_{i \in n, n \leq N} Area_{Di}}{\sum_{j \in m, m \leq M} Area_{Rj}}$$

or $$Ratio_{Multi}\_Re\_Depolar_{mn} = \frac{\sum_{j \in m, m \leq M} Area_{Rj}}{\sum_{i \in n, n \leq N} Area_{Di}}$$

In which, $Area_{Di}$, $Area_{Rj}$, $Area_{Ri}$, and $Area_{Dj}$ are segmented level area partitions in depolarization and repolarization signal portions either within one cardiac cycle or in different heart cycles, n and m are a selected number of amplitude partition areas within selected depolarization and repolarization signal portions, respectively. Areas within a selected signal portion are selected based on clinical application and/or user command and they do not need to be sequential. In 10 amplitude level partitions selected partitions may comprise partition areas #2, #6, #10, for example. N and M are total number of the segmented areas in the depolarization and repolarization process signal portions, respectively. Segmented depolarization and repolarization signal portions may be electrophysiological signals from a left or right atrial chamber, left or right ventricular chamber, or may be hemodynamic or vital signal waveform signal partitions, such as associated with contracting and reperfusion processes in systolic and diastolic procedures.

System 10 performs bilateral and unilateral depolarization-repolarization pattern ratio analyses using the area or volume based ratio calculation. The pattern ratios are computed using different parameters, including timing, energy, frequency distribution, entropy and complexity, for example, within segmented signal waveform portions. The system in one embodiment automatically selects different pattern calculations in response to data indicating a clinical application and environment noise, for example. Pattern ratio calculations (using unilateral or bilateral ratio calculations) include, Energy based depolarization-repolarization pattern ratio, $$Ratio_{Multi}\_Re\_Depolar_{mn}|_{Energy} = \frac{\sum_{j \in m, m \leq M} Energy_{Rj}}{\sum_{i \in n, n \leq N} Energy_{Di}}$$

In which the $Energy_{xj}$ is the total energy of the corresponding segmented elements. Entropy based depolarization-repolarization pattern ratio, $$Ratio_{Multi}\_Re\_Depolar_{mn}|_{Entropy} = \frac{\sum_{j \in m, m \leq M} Entropy_{Rj}}{\sum_{i \in n, n \leq N} Entropy_{Di}}$$

In which the $Entropy_{xj}$ is the entropy of corresponding segmented signal portion elements.

Figure 3:
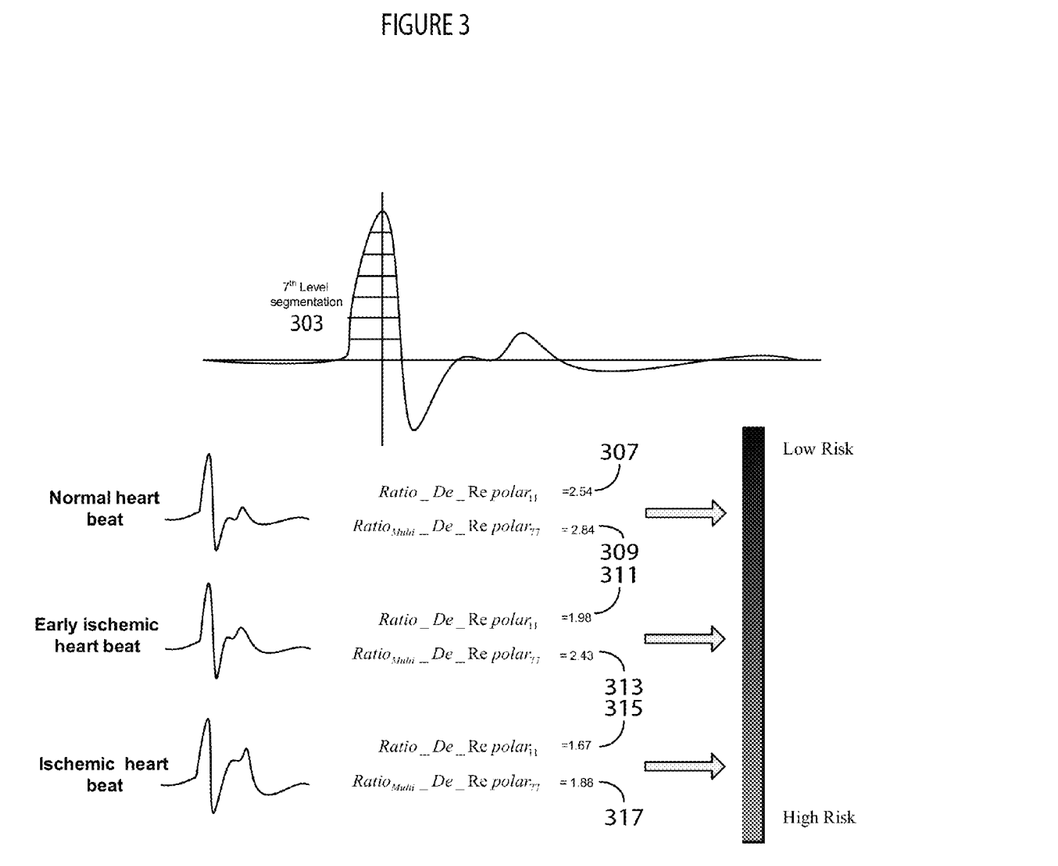
FIG. 3 shows a QRS complex waveform signal portion segmented into 7 levels and depolarization-repolarization ratio analyses performed for cardiac signals in different normal, early ischemic and ischemic episodes, according to invention principles.

FIG. 3 shows a cardiac QRS complex waveform signal portion segmented into 7 levels (303) and depolarization-repolarization ratio analyses performed for normal, early ischemic and ischemic episodes. Different pattern ratios are utilized in different clinical applications in response to required sensitivity and accuracy of pattern analysis. Predetermined validation and arrhythmia detection ratio thresholds provide quantitative and qualitative diagnosis. Ratios Ratio_De_Re epolar$_{11}$ and Ratio$_{Multi}$_De_Re polar$_{77}$ are selected based on medical application and are determined for normal, early ischemic and ischemic episodes. Myocardial ischemia events are detected (usually associated with coronary arteries and vessels in a ventricular portion) and a QRS complex waveform portion is utilized for calculation of ventricular depolarization and repolarization signal portion ratios. The 7-Level amplitude partitions 303 are used for improved diagnosis sensitivity and reliability. The system automatically adaptively selects number of levels and associated partitions for desired analysis sensitivity, reliability, stability and usability. The calculated Ratio_De_Re epolar$_{11}$ and Ratio$_{Multi}$_De_Re polar$_{77}$ for QRS based ventricular depolarization-repolarization analysis comprise 2.54 and 2.84 (307, 309) for a normal signal episode, 1.98 and 2.43 (311, 313) for early myocardial ischemia episode and 1.67 and 1.88 (315, 317) for a myocardial ischemia episode. High and low risk thresholds are predetermined for depolarization-repolarization ratio analysis for early warning of cardiac events. A calculated parameter is used to determine cardiac condition severity level, such as Ratio_De_Re epolar$_{11}$ value that varies from 2.54 (normal case) to 1.67 (MI case) showing a change of approximately 34%. A threshold is set for different levels of arrhythmia, MI such as 10%, 20%, for example. Different statistical analysis methods are used, including student test, two-tail hypothesis test, for example, to quantitatively characterize pattern ratio variability and variation. The statistical analysis improves clinical diagnosis performance and lowers incidence of false alarms.

Figure 4:
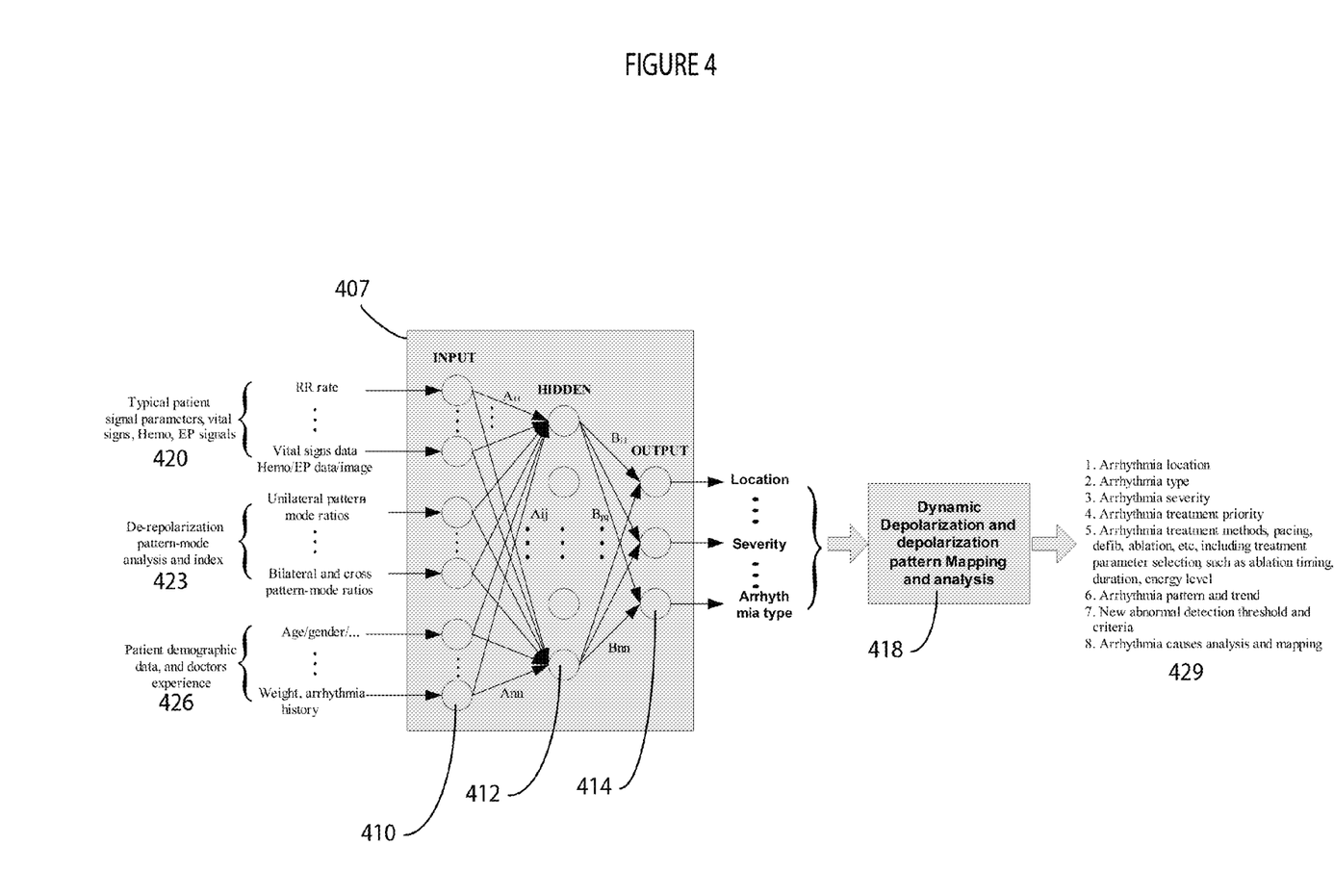
FIG. 4 shows an artificial neural network (ANN) for cardiac depolarization and repolarization pattern analysis, according to invention principles.

FIG. 4 shows artificial neural network (ANN) 407 for nonlinearly deriving information based on a combination of multiple input parameters for cardiac depolarization and repolarization pattern analysis. Different pattern ratios are utilized together to localize position of arrhythmia, timing (such as in a depolarization or repolarization ECG cycle portion), cardiac pathology type, cardiac arrhythmia severity and potential treatment methods, for example. Different ratio combinations may alternatively be determined using a fuzzy system or expert system. ANN unit 407 structure comprises 3 layers, an input layer 410, hidden layer 412 and output layer 414. ANN unit $A_{ij}$ weights are applied between input layer 410 and hidden layer 412 components of the ANN computation and $B_{pq}$ weights are applied between hidden layer 412 and calculation components 414 of the ANN computation. The $A_{ij}$ weights and $B_{pq}$ weights are adaptively adjusted and tuned using a training data set. ANN unit 407 incorporates a self-learning function that processes signals 420, 423 and 426. The ANN depolarization-repolarization pattern ratio calculation combines patient vital signs, image data, hemodynamic data and ECG, ICEG data 420, depolarization-repolarization pattern ratios 423 and patient demographic data and medical history 426 to map depolarization-repolarization ratios to a medical condition 418 and identify arrhythmia location, severity, type, treatment priority, trend, pattern, pacing ablation and defibrillation parameters and update of an arrhythmia detection threshold 429. The depolarization-repolarization pattern ratio based cardiac arrhythmia analysis includes different kinds of patient and signal parameter in a ratio calculation, including amplitude level partition area, energy, timing and spectrum distribution parameters, for example.

Figure 5:
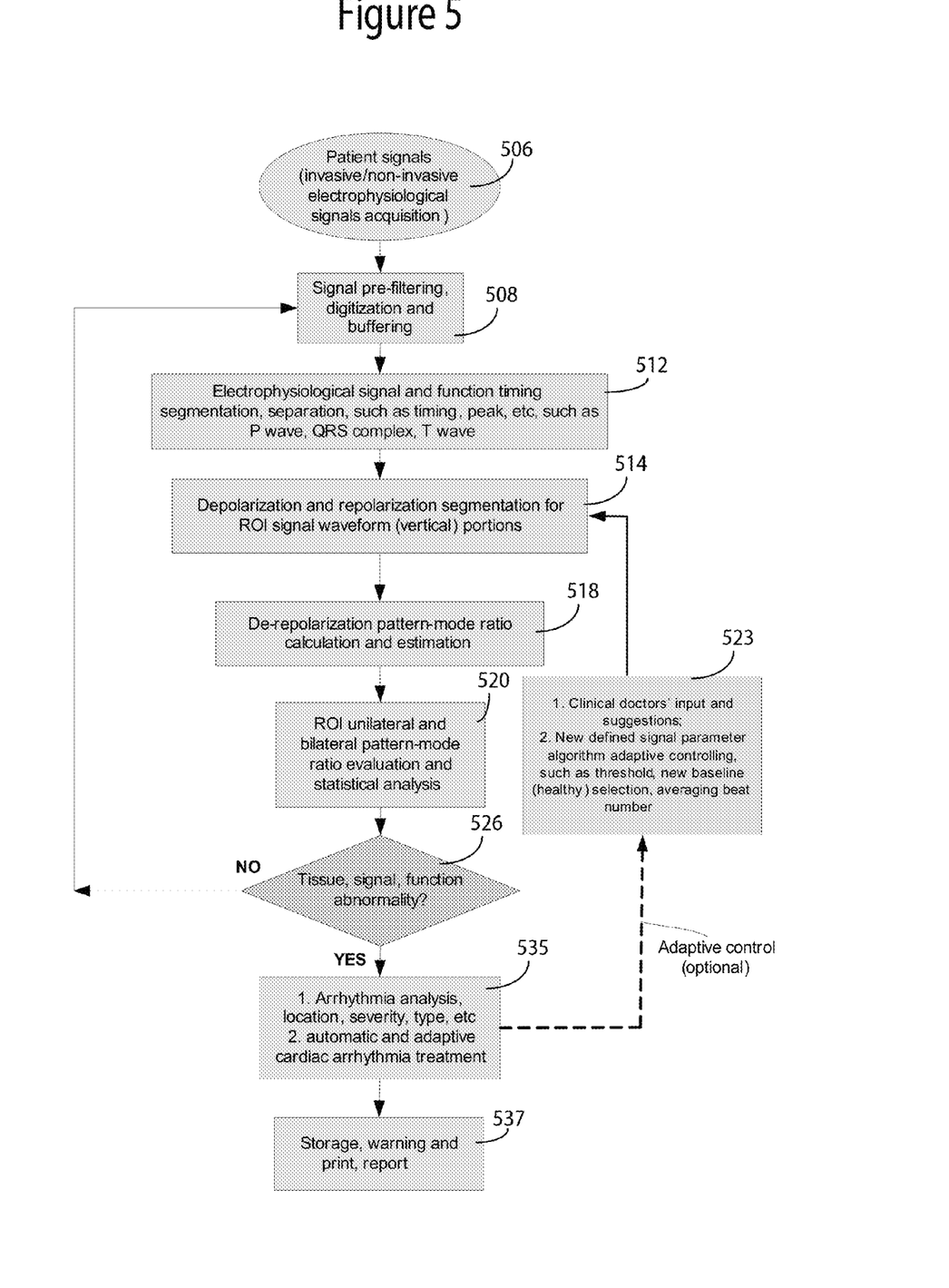
FIG. 5 shows a flowchart of a process for unilateral and bilateral depolarization/repolarization pattern ratio analysis for cardiac arrhythmia detection and characterization, according to invention principles.

FIG. 5 shows a flowchart of a process performed by system 10 (FIG. 1) for unilateral and bilateral depolarization/repolarization pattern ratio analysis for cardiac arrhythmia detection and characterization. Interface 12 buffers and digitizes a non-invasive blood pressure amplitude signal, blood oxygen saturation (SPO2) signal, surface ECG signal, ICEG signals, vital signs signals in step 508 received in step 506. Interface 12 in step 508 filters the received signal data using a filter adaptively selected in response to data indicating clinical application to remove patient movement and respiratory artifacts as well as power line noise. In step 512 signal processor 15 performs signal segmentation, such as of, P, Q, R, S, T, U waves in electrophysiological signals using a known peak detector and by identifying peaks of signals by segmenting a signal represented by sampled data into windows where the waves are expected and by identifying the peaks within the windows, as previously described.

Processor 15 in step 514 identifies depolarization and repolarization segments of the received sampled signal data and partitions the identified depolarization and repolarization segments into a number of amplitude level partitions. Processor 15 selects the number of partitions in response to data identifying a clinical procedure being performed. In step 518, processor 15 determines areas under the sampled signal data waveform of corresponding amplitude level partitions. Processor 15 in step 520 derives parameters in response to the determined partition areas for multiple different heart cycles of the same patient. Processor 15 calculates the previously described ratios and performs a statistical evaluation by calculating variation in the calculated ratios as newly acquired data from current heart cycles is processed. The statistical evaluation and threshold comparison for cardiac arrhythmia detection and location, severity characterization, are used to control and adjust a treatment device such as a defibrillator, ablation or pacing device and user warning module. Processor 15 performs depolarization-repolarization unilateral and bilateral pattern ratio calculation by averaging derived data across multiple heart cycles to decrease noise and artifact effects. System 10 adaptively controls and adjusts an averaging window. In one embodiment, processor 15 derives a ratio of a determined first area of an individual amplitude level to a sum of multiple amplitude level areas under the waveform in a selected signal portion. Processor 15 in other embodiments, derives the ratio in response to at least one of, an energy, frequency, entropy and complexity value associated with the determined first area of an individual amplitude level.

Processor 15 in step 526 uses a repository of mapping information, associating ranges of the derived ratios with corresponding medical conditions and compares the derived ratios with the ranges to identify a medical abnormality. In response to determining a normal medical condition, processor 15 updates the calculation by iteratively repeating the process from step 508 using new input data over one or more heart cycles. In response to a detected abnormality, processor 15 in step 535 identifies arrhythmia, location, type and severity and automatically adaptively determines cardiac arrhythmia treatment using predetermined mapping information. Processor 15 uses predetermined mapping information that associates ranges of derived ratios with particular patient demographic characteristics and with corresponding medical conditions and the system uses patient demographic data including at least one of, age weight, gender and height in comparing a derived ratio with the ranges. Output processor 19 generates an alert message in step 537 indicating a potential medical condition and stores determined ratios in repository 17. Processor 15 in step 523 adaptively adjusts a time window, window shift step, the number of samples in a calculation window used for calculation from step 514 and adjusts the selected portion of a filtered signal processed and adjusts a threshold employed by processor 15 to improve abnormality detection.

Figure 6:
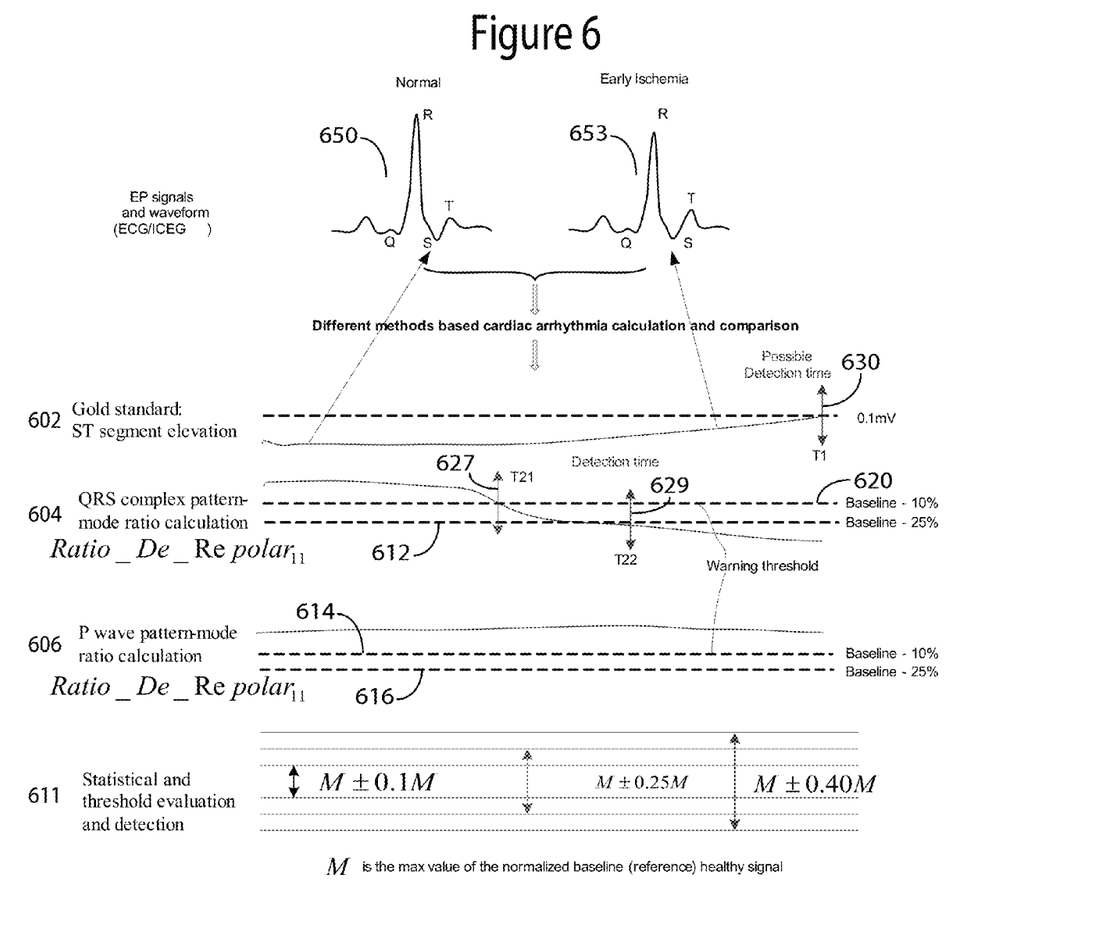
FIG. 6 shows a simulated calculation for myocardial ischemia analysis using depolarization-repolarization pattern ratio analysis, according to invention principles.

FIG. 6 shows a simulated calculation for myocardial ischemia analysis using depolarization-repolarization pattern ratio analysis. Pattern ratio analysis for normal 650 and myocardial ischemia 653 events is compared with standard ST segment analysis 602. In order to detect coronary myocardial ischemia, ST segment voltage displacement (e.g. exceeding 0.1 mV elevation) is utilized to quantify a myocardial ischemia event. However ST segment voltage change fails to indicate severity of ischemia events and other pathology. Signal processor 15 performs QRS complex pattern ratio analysis 604 and P wave depolarization-repolarization analysis 606. Processor 15 performs a simple statistical evaluation, using 10%, 25% thresholds for depolarization-repolarization pattern ratio analysis. The system improves early myocardial ischemia event detection and characterization for cardiac arrhythmia location, type and severity determination.

Signal processor 15 (FIG. 1) uses predetermined baseline −10% (620, 614) and −25% thresholds (612, 616) for QRS complex waveform depolarization-repolarization pattern ratio 604 and P wave depolarization-repolarization pattern ratio analysis 606. The thresholds are also used for ischemia event severity level analysis. Processor 15 compares normal and early ischemia cardiac signal episodes. The ST segment 602 detects a myocardial ischemia event at time T1 630 while QRS complex waveform based bilateral ratio analysis Ratio_De_Re polar$_{11}$ 604 detects the myocardial ischemia event at T21 627 (with 10% change threshold) or T22 629 (with 25% change threshold). T21 occurs about 10 seconds earlier than T22 while T21 is 45 seconds earlier than T1. The P wave depolarization-repolarization pattern ratio Ratio_De_Re polar$_{11}$ 606 is also calculated and the results show there is not too much change (<2% deviation) for a P wave portion. This indicates cross comparison utilized for heart portion and arrhythmia location, severity and type analysis. Electrophysiological signal unilateral and bilateral depolarization-repolarization calculations are used for cardiac arrhythmia detection to identify cardiac disorders, differentiate cardiac arrhythmias, characterize pathological severity, predict life-threatening events. The system may be used in a bedside cardiac monitoring system or portable patient cardiac function monitoring and analysis system, such as a Holster Monitoring and ICD device.

Figure 7:
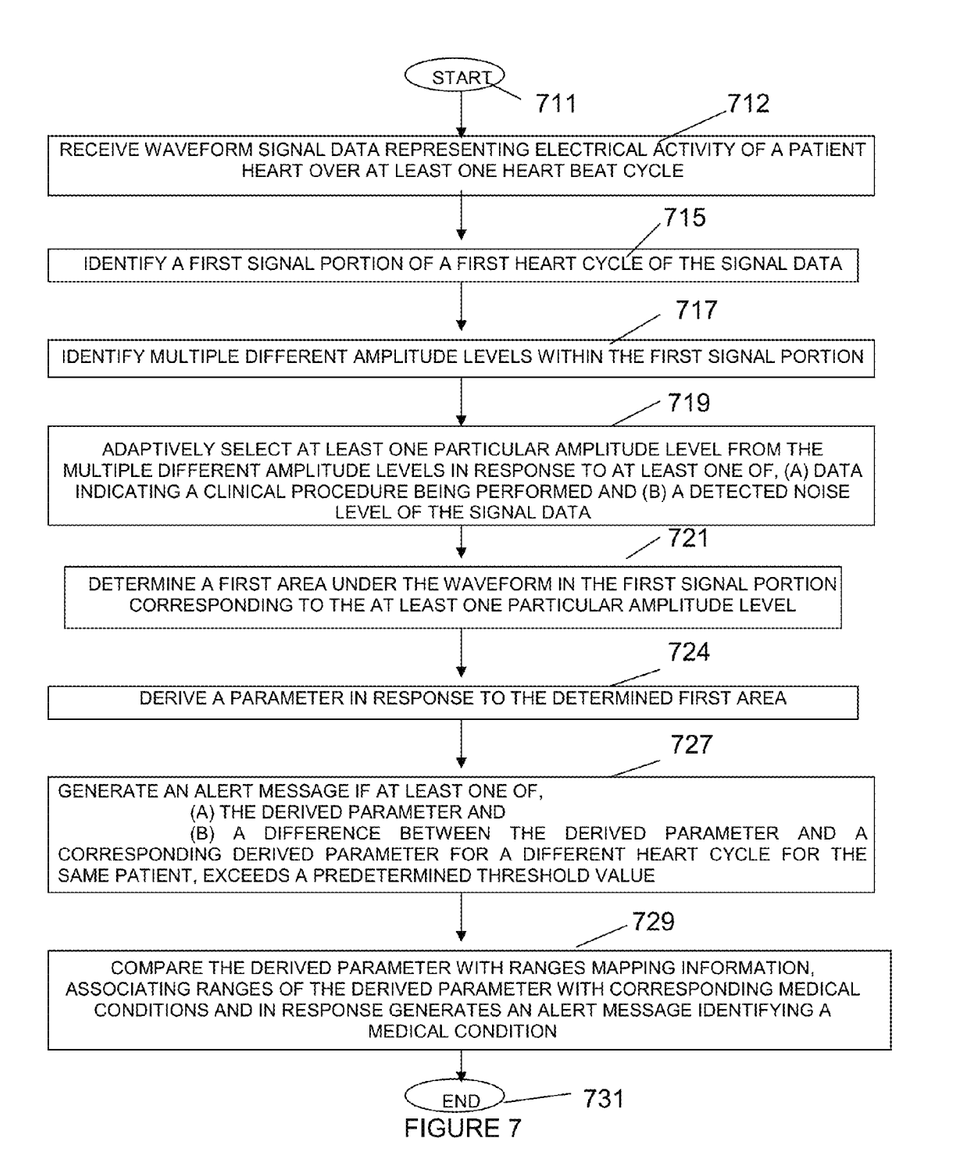
FIG. 7 shows a flowchart of a process used by a system for heart performance characterization and abnormality detection, according to invention principles.

FIG. 7 shows a flowchart of a process used by system 10 (FIG. 1) for heart performance characterization and abnormality detection. In step 712 following the start at step 711, interface 12 receives waveform signal data representing electrical activity of a patient heart over at least one heart beat cycle and comprising digitally sampled data. In step 715 signal processor 15 employs a signal peak and amplitude detector for identifying a first signal portion of a first heart cycle of the signal data and in step 717 identifies multiple different amplitude levels within the first signal portion. The signal peak detector, detects peaks of a waveform within the received signal data and a valley as a negative peak in the waveform. The signal peak detector detects a baseline comprising a substantially zero voltage level of the signal data by filtering out a static (DC) voltage signal component from the received signal data and by determining a substantially zero voltage level of the resultant filtered received signal data and detects a signal portion as lying between at least one of, a peak, a valley and an intersection of the waveform with the baseline.

Processor 15 in step 719, adaptively selects the at least one particular amplitude level from the multiple different amplitude levels in response to at least one of, (a) data indicating a clinical procedure being performed and (b) a detected noise level of the signal data. In step 721, processor 15 determines a first area under the waveform in the first signal portion corresponding to at least one particular amplitude level partition and in step 724 derives a parameter in response to the determined first area. A timing detector in processor 15 detects time duration between a detected peak of a heart activity signal of the patient and a detected peak of the received signal data of the patient.

Signal processor 15 derives the parameter as a ratio of the determined first area of an individual amplitude level to a sum of multiple amplitude level areas under the waveform in the first signal portion. In one embodiment signal processor 15 derives the parameter in response to at least one of, energy, frequency, entropy and complexity values associated with at least one of the determined first area of an individual amplitude level and a sum of multiple amplitude level areas under the waveform in the first signal portion. In a further embodiment, signal processor 15 derives the parameter in response to calculating a standard deviation or variance of the determined first area over multiple heart cycles. In an embodiment, processor 15 identifies a different second signal portion of a first heart cycle of the signal data, identifies multiple different amplitude levels within the second signal portion, determines a second area under the waveform in the second signal portion corresponding to at least one particular amplitude level and derives the parameter in response to the determined first and second areas, e.g., as a ratio of the determined first area and determined second area. The first signal portion substantially comprises a QR portion and the second signal portion substantially comprises an RS portion and the first signal portion and the second signal portion are in the same heart cycle or different heart cycles of the same patient.

Output processor 19 in step 727 generates an alert message if at least one of, (a) the derived parameter and (b) a difference between the derived parameter and a corresponding derived parameter for a different heart cycle for the same patient, exceeds a predetermined threshold value. The threshold value is derived from received signal data for a population of patients having similar demographic characteristics including at least two of, (a) age, (b) weight, (c) gender and (d) height, to those of the patient. Signal processor 15 dynamically adjusts the threshold value in response to a determined sensitivity of arrhythmia detection. In step 729 processor 15 stores mapping information in repository 17, associating ranges of the derived parameter with corresponding medical conditions and output processor 19 compares the derived parameter with the ranges and in response generates an alert message identifying a medical condition. The predetermined mapping information associates ranges of derived parameters with particular patient demographic characteristics and with corresponding medical conditions and the system uses patient demographic data including at least one of, age weight, gender and height in comparing a derived parameter with the ranges and generating an alert message indicating a potential medical condition. The process of FIG. 7 terminates at step 731.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display elements or portions thereof. A user interface comprises one or more display elements enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display elements, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the elements for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display elements in response to signals received from the input devices. In this way, the user interacts with the display elements using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. A histogram of an image is a graph that plots the number of pixels (on the y-axis herein) in the image having a specific intensity value (on the x-axis herein) against the range of available intensity values. The resultant curve is useful in evaluating image content and can be used to process the image for improved display (e.g. enhancing contrast).

The system and processes of FIGS. 1-7 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system detects timing, frequency and energy changes in ECG and intra-cardiac electrograms, to identify and characterize cardiac repolarization and depolarization patterns by calculating ratios including a time-spatial ratio, area ratio and energy ratio between a repolarization portion and depolarization portion within the same heart beat, for detection of early stage atrial fibrillation and myocardial ischemia-infarction, for example. Further, the processes and applications may, in alternative embodiments, be located on one or more (e.g., distributed) processing devices on a network linking the units FIG. 1. Any of the functions and steps provided in FIGS. 1-7 may be implemented in hardware, software or a combination of both. No claim element herein is to be construed under the provisions of 35 U.S.C. 112, sixth paragraph, unless the element is expressly recited using the phrase "means for."

What is claimed is:

1. A system for heart performance characterization and abnormality detection, comprising:
   an interface for receiving waveform signal data representing electrical activity of a patient heart over at least one heart beat cycle;
   a signal processor, employing a signal peak and amplitude detector and
      identifying a first signal portion of a first heart cycle of said signal data,
      identifying a plurality of different amplitude ranges within said first signal portion,
      determining a first area under said waveform in said first signal portion and in only one of the plurality of different amplitude ranges, and
      deriving a parameter based on the determined first area; and
   an output processor for generating an alert message if at least one of,
      (a) the derived parameter and
      (b) a difference between the derived parameter and a corresponding derived parameter for a different heart cycle for the patient, exceeds a predetermined threshold value.

2. A system according to claim 1, wherein
said signal data is digitally sampled data and
said first signal portion substantially comprises at least one of, (a) a QR portion and (b) an RS portion.

3. A system according to claim 1, wherein
said signal peak detector,
detects peaks of a waveform within the received signal data and a valley as a negative peak in the waveform and
detects a baseline comprising a substantially zero voltage level of the signal data by filtering out a static (DC) voltage signal component from the received signal data and by determining a substantially zero voltage level of the resultant filtered received signal data and
detects a signal portion as lying between at least one of, a peak, a valley and an intersection of said waveform with said baseline.

4. A system according to claim 1, wherein
said signal processor derives said parameter as a ratio of the determined first area to a sum of areas under said waveform in said first signal portion in one or more others of the plurality of amplitude ranges.

5. A system according to claim 1, wherein
said signal processor derives said parameter in response to at least one of, an energy, frequency, entropy and complexity value associated with said determined first area.

6. A system according to claim 1, wherein
said signal processor derives said parameter in response to at least one of, energy, frequency, entropy and complexity values associated with both said determined first area and a sum of areas under said waveform in said first signal portion in one or more others of the plurality of amplitude ranges.

7. A system according to claim 1, wherein
said signal processor derives said parameter in response to calculating a standard deviation or variance of said determined first area over a plurality of heart cycles.

8. A system according to claim 1, wherein
said signal processor
identifies a second signal portion of the first heart cycle of said signal data,
identifies a second plurality of different amplitude ranges within said second signal portion,
determines a second area under said waveform in said second signal portion and in only one of the plurality of different amplitude ranges, and
derives said parameter based on the determined first and second areas.

9. A system according to claim 8, wherein
said first signal portion substantially comprises a QR portion and said second signal portion substantially comprises an RS portion.

10. A system according to claim 8, wherein
said first signal portion and said second signal portion are in the same heart cycle.

11. A system according to claim 8, wherein
said first signal portion and said second signal portion are in different heart cycles of the same patient.

12. A system according to claim 8, wherein
said signal processor derives said parameter as a ratio of the determined first area and determined second area.

13. A system according to claim 1, wherein
said signal processor adaptively selects said of the plurality of different amplitude ranges from said plurality of different amplitude ranges in response to at least one of, (a) data indicating a clinical procedure being performed and (b) a detected noise level of said signal data.

14. A system according to claim 1, wherein
said signal processor includes a timing detector for detecting time duration between a detected peak of a heart activity signal of the patient and a detected peak of the received signal data of the patient.

15. A system according to claim 1, wherein
said threshold value is derived from received signal data for a population of patients.

16. A system according to claim 15, wherein
said population of patients has similar demographic characteristics including at least two of, (a) age, (b) weight, (c) gender and (d) height, to those of said patient.

17. A system according to claim 1, wherein
said signal processor dynamically adjusts said threshold value in response to a determined sensitivity of arrhythmia detection.

18. A system according to claim 1, including
a repository of mapping information, associating ranges of said derived parameter with corresponding medical conditions and said output processor compares said derived parameter with said ranges and in response generates an alert message identifying a medical condition.

19. A system according to claim 18, wherein
said predetermined mapping information associates ranges of derived parameters with particular patient demographic characteristics and with corresponding medical conditions and said system uses patient demographic data including at least one of, age weight, gender and height in comparing a derived parameter with said ranges and generating an alert message indicating a potential medical condition.

20. A system for heart performance characterization and abnormality detection, comprising:
an interface for receiving waveform signal data representing electrical activity of a patient heart over at least one heart beat cycle;
a signal processor, employing a signal peak and amplitude detector, and
identifying a first signal portion of a first heart cycle of said signal data,
identifying a second signal portion of the first heart cycle of said signal data,
identifying a plurality of different amplitude ranges within the first and second signal portions,
determining a first area under said waveform in said first signal portion and in only one of the plurality of different amplitude ranges,
determining a second area under said waveform in said second signal portion and in only the one of the plurality of different amplitude ranges, and
deriving a parameter based on the determined first and second areas; and
an output processor for generating an alert message if at least one of,
(a) the derived parameter and
(b) a difference between the derived parameter and a corresponding derived parameter for a different heart cycle for the patient, exceeds a predetermined threshold value.

21. A system according to claim 20, wherein
said first signal portion substantially comprises a QR portion and said second signal portion substantially comprises an RS portion and
said first signal portion and said second signal portion are at least one of, (a) in the same heart cycle and (b) in different heart cycles of the same patient.

* * * * *